Figure 1:
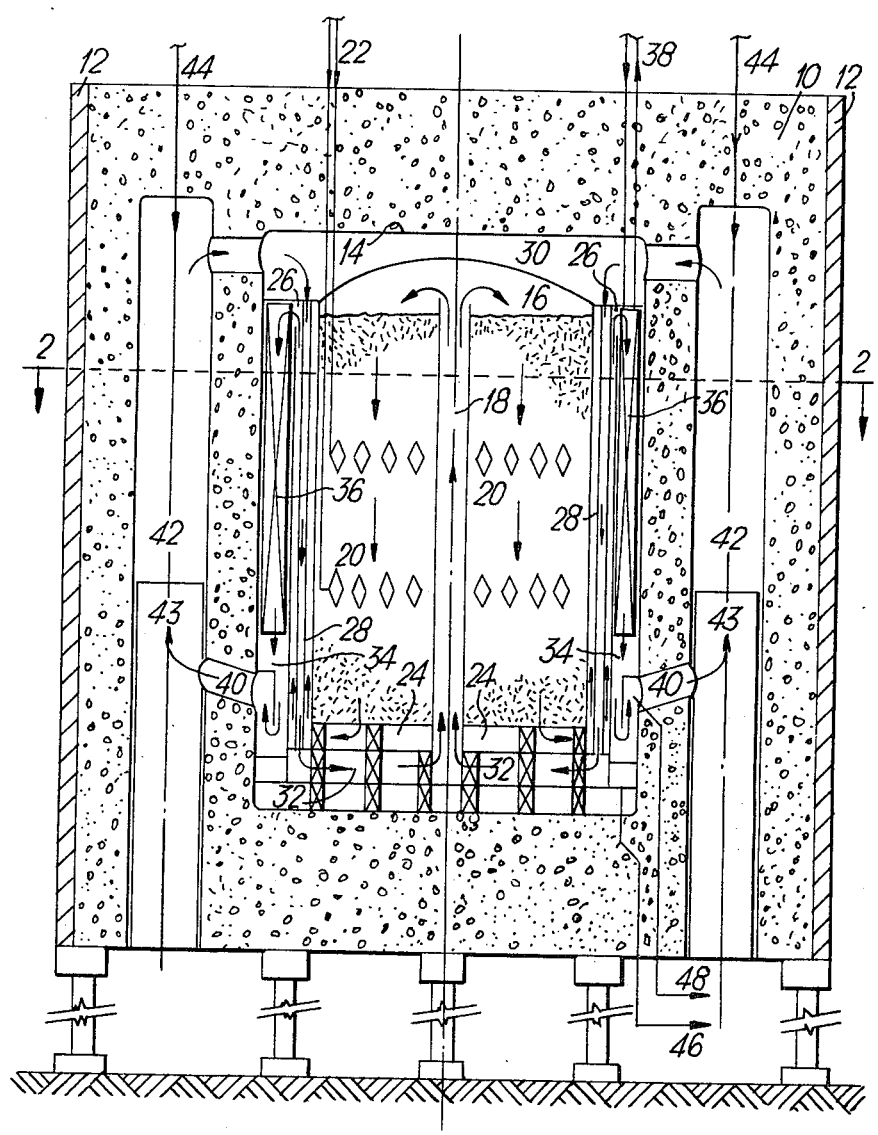

United States Patent [19]
Ciechowski

[11] 3,957,449
[45] May 18, 1976

[54] SYNTHESIS PLANT

[75] Inventor: Franciszek Ciechowski, Stockton-on-Tees, England

[73] Assignee: Imperial Chemical Industries Limited, London, England

[22] Filed: Jan. 9, 1975

[21] Appl. No.: 539,740

Related U.S. Application Data

[63] Continuation of Ser. No. 335,112, Feb. 23, 1973, abandoned.

[30] Foreign Application Priority Data

Feb. 28, 1972 United Kingdom................ 9034/72

[52] U.S. Cl................................ 23/289; 23/288 K; 23/288 M; 260/449.5; 423/360
[51] Int. Cl.² .................... B01J 8/02; C01C 1/04; C07C 29/16
[58] Field of Search............ 23/288 K, 289, 288 M; 176/38; 423/360; 260/449.5

[56] References Cited
UNITED STATES PATENTS

| | | |
|---|---|---|
| 1,335,891 | 4/1920 | Greenwood et al............... 23/288 K |
| 1,839,738 | 1/1932 | Casale................................. 23/289 |
| 3,228,849 | 1/1966 | Fellows.............................. 176/39 |
| 3,475,272 | 10/1969 | Fortescue et al. ................ 176/38 X |
| 3,694,169 | 9/1972 | Fawcelt et al. ........................ 23/289 |

Primary Examiner—James H. Tayman, Jr.
Attorney, Agent, or Firm—Cushman, Darby & Cushman

[57] ABSTRACT

A plant for producing, eg ammonia or methanol by catalytic synthesis at superatmospheric temperature and pressure comprises a vessel equipped internally with all the high-temperature units required for the synthesis, namely means for heating synthesis gas to synthesis inlet temperature, admitting it to the catalyst, withdrawing it and cooling it. Preferably all the high-pressure units are also inside the vessel. The plant makes possible extremely high outputs of product, such as 8000 metric tons per day.

4 Claims, 2 Drawing Figures

SYNTHESIS PLANT

This is a continuation of application Ser. No. 335,112, filed Feb. 23, 1973, and now abandoned.

This invention relates to plants and processes for synthesis, particularly of methanol or ammonia.

Recent suggestions to use methanol as a fuel, either as such or after conversion to e.g. methane, have posed the problem of how to produce it on a scale substantially larger than has been required in the chemical industry. There is a continuing demand for ammonia at the lowest possible prices, for agricultural and other industrial uses. It is however impracticable to scale up know plants substantially since this requires ducts so large in diameter (e.g. 1.5 m) that the usual measures to deal with expansion and contraction with temperature changes cannot be used. Especially when, as has been proposed, such synthesis plants are to operate at oilfields and gas fields, it becomes prohibitively difficult to transport the very large vessels to the site. Fabrication of such vessels and assembly of ducts and pipework cannot, moreover, be efficiently done at sites far from centres of engineering expertise.

We have now devised plants and processes in which these difficulties are substantially decreased.

According to the invention a plant for carrying out synthesis reactions in the gas phase at superatmospheric pressure and temperature comprises a vessel capable of withstanding the pressure required for the sythesis, having means for admitting fresh synthesis gas and for passing reacted gas to means for product recovery, and equipped internally with means for heating synthesis gas to synthesis inlet temperature, for admitting it to one or more beds for synthesis catalyst and for withdrawing reacted gas from the catalyst bed and cooling it.

Thus all the items of equipment operated at temperatures substantially above atmospheric are inside the vessel; consequently gas flow connections are short and do not present thermal expansion difficulties. Preferably also the means for product recovery and any means (as described below) for recycling unreacted gas to the catalyst are also inside, that is, all the high-pressure gas flow connections (with the exception of the fresh synthesis gas feed) are inside. Consequently all the equipment that in a present-day plant is constructed as single high-pressure items fabricated in steel and individually located on a site linked by ducts can be low-pressure items arranged compactly together in the single outer vessel.

The fresh synthesis gas feed and product recovery ducts are relatively small pipes at low temperatures and thus not subject to unprecedented thermal expansion difficluties. The same applies to ducts for supplying coolant or scrubbing fluid to the means for product recovery and for purge gas withdrawal.

The means for heating synthesis gas and, after reaction, cooling it, includes preferably a feed/effluent heat exchanger, unless the plant is required at a site where fuel is cheap and expendible coolant or other cheap cooling is available. The heat exchanger can be disposed in any convenient manner, such as in known reactors for synthesis, but preferably occupies an annular-section spaced about the catalyst bed or beds, thus making it possible to have a largely unobstructed catalyst bed or beds. The means for product recovery may comprise a further heat exchanger and a gas/liquid separator. It is preferably disposed in an annular-section space about the feed/effluent heat exchanger. Suitably this heat exchanger comprises cooling pipes fed from outside with coolant liquid. By this symmetrical annular disposition of cooler and cooler spaces it is possible to prevent the vessel walls from becoming overheated; however further measures, such as a cavity carrying cold feed gas or an insulating layer or both may be used instead or in addition.

If the vessel is a concrete pressure vessel as described below, the heating means or coolers or both can be in chambers in the vessel walls.

If the process to be operated involves recycle of unreacted synthesis gas to the catalyst after separation of product from it, a gas flow connection is provided from the product recovery means to one or more circulators, and thence to the heating means. Each circulator may be, since the gas after product recovery is cool, disposed outside the vessel. Preferably, however, it is wholly within the vessel or in a compartment separate from the main chamber of the vessel but connected thereto by a short duct, for example it may be in a compartment in the wall of a concrete pressure vessel. The driving engine for each circulator is preferably outside the vessel or such compartment in order to facilitate maintenance and also to simplify the disposal of the effluent of the engine if it is a combustion engine or steam turbine.

For use in a recycle process the vessel is provided with a "purge" outlet, suitably at the inlet side of each circulator. This is because the concentrations of unreactive components of the synthesis gas, which usually include methane (in methanol or ammonia synthesis) and nitrogen and noble gases (in ammonia synthesis), and also any reacting gases in excess of stoichiometric quantities, gradually build up and must be kept down to levels at which the reacting gases are not excessively diluted.

In recycle synthesis processes it is usual for the rate of flow of total synthesis gas to be substantially more, for example 4–12 times more in methanol synthesis and 3–6 times more in ammonia synthesis, than the rate of flow of fresh synthesis gas. In the plant for such processes, therefore, the recycle ducts would have to be especially large in diameter if the process were scaled up substantially. Furthermore, since the pressure-drop through long external recycle ducts would be especially large owing to the high rate of flow of gas, the short ducts of plants according to the invention make possible a substantial saving in power consumption, especially at the relatively low pressures which are desirable in the present state of development of very large pressure vessels. Alternatively a greater recycle rate and consequently more complete conversion of fresh synthesis gas can be achieved at conventional power consumption rate. Taking also into account the possibility of using a relatively wide, shallow catalyst bed, recycle rates up to 20 and even higher can be envisaged for methanol synthesis or ammonia synthesis.

For temperature control the catalyst bed or beds can be of the quench-cooled, tube-cooled or coolant-cooled type. A very convenient plant using quench-cooling comprises a single catalyst bed equipped with means for temperature control comprising at least one set of perforated hollow bars disposed transversely to the gas flow direction, each having associated with it a sparger or equivalent device for injecting cool gas, the hollow bars being large enough in cross section for their interiors to constitute mixing zones and close enough together or to the catalyst bed walls to cause a substantial proportion of reaction mixture to pass through their interiors. The hollow bars are far enough apart and from the bed walls to alloy catalyst to pass during charging or discharging; and naturally the perforations are small enough to prevent catalyst entering. Various bar arrangements can be used, for example, secantial, circumferential or radial, and several sets can be disposed successively in the gas flow direction. Such a quench-cooled reactor is the subject of our U.K. Pat. No. 1,105,614 and corresponding patents in other countries.

If the catalyst is disposed in several beds in parallel, quench fluid injection or feed/effluent heat exchange or contact with coolant can be effected between the beds. If cooling by coolent is employed, this may be by boiling water, owing to the efficiency with which heat is removed. For this purpose the whole catalyst bed or each catalyst bed may be disposed in boiler tubes or in the space around such tubes, or boiler tubes may be disposed within or between catalyst beds. It will be appreciated that a number of temperature control methods can be used in combination.

If it is desired to keep down the pressure-drop through the catalyst bed, the gas flow can be perpendicular to the longest direction of the bed or can be convergent, as described in our U.K. specification No. 1,307,845, for example.

In order to provide the large reactor volume required for very large outputs, for example 8,000 metric tons of methanol or ammonia per day, the vessel shell is preferably made of concrete, suitably in the form of interlocking blocks or of a unitary shell held together by pre-stresed metal members, for example, tie rods, bands and wires. Such vessels have been built for containing nuclear reactors, in volumes of the order of 2500 m$^3$, and to withstand internal pressures in the range 40 to 60 ata. Vessels of this type have been designed with a number of compartments, for example, 6, arranged about a main interior chamber. These compartments conveniently house the circulator or circulators if a recycle plant is used. The annular disposition of the heat exchanger is very suitable for a concrete vessel, since over-heating of the concrete is then easier to prevent. A suitable vessel is that used for the "Hartlepool" reactor or proposed for the "HTR" reactor, and described in the article by J. D. McKean in "Nuclear Engineering International," September 1969, pages 724–730, in an article in the November 1969 issue of the same journal and in the article by J. A. Dunster in "Concrete", June 1970, pages 260–264.

The pressure of methanol synthesis is conveniently less than 150 ata, especially less than 120 ata, for example 30–80 ata, in order to use a vessel shell similar to what is at present available. The temperature is suitably under 300°C, for example in the range 190°–270°C. These conditions afford acceptable outputs of methanol when a copper-containing catalyst is used. Such catalysts usually also contain zinc oxide and/or one or more oxides such as those of aluminum, chromium, manganese, magnesium and vanadium. Suitable processes using copper-containing catalysts are described in our U.K. Pats. Nos. 1,010,871, 1,059,035 and 1,296,212.

Ammonia synthesis in the plant according to the invention is preferably at pressures under 200 ata, especially 40–120 ata, so as again to use a vessel shell similar to what is at present available.

It is expected that vessels of the concrete type mentioned above will be developed to withstand higher and higher pressures during the term of any patent granted on this application, hence the preferred pressures are likely to increase correspondingly. In any event, however, the plant according to the invention will have the advantage over previously proposed plants that higher circulation rates corresponding to accordingly lower pressures and lower pass conversions will be tolerable.

The source of methanol synthesis gas for the process is suitably a hydrocarbon/steam reaction process operated at a suitably high outlet temperature. Conventiently it is a tubular steam-reforming process fed with natural gas, without or with addition of carbon dioxide to the reforming stage or to the methanol synthesis, and without or with a non-tubular oxidative secondary reforming stage. As an alternative the feedstock may be a higher hydrocarbbon such as a naphtha, in which event simple tubular reforming may be used, or methane-rich gas formation followed by endothermic hydrocarbon/steam reaction. Alternatively various types of partial oxidation may be used, using air, oxygen or enriched air as the oxidant, and without or with a catalyst. More than one source of synthesis gas may be used.

When the methanol synthesis catalyst is to be of the copper type it is unnecessary to remove carbon dioxide from the gas unless the gas would otherwise be substantially deficient in hydrogen, and it is preferable to leave at least carbon dioxide in the gas to a partial pressure of at least 0.5 ata.

The source of ammonia synthesis gas may be the same as that of methanol synthesis gas, in combination with subseaquent known stages to minimise the methane content of the gas, to introduce nitrogen and to remove carbon oxides.

Figure 2:
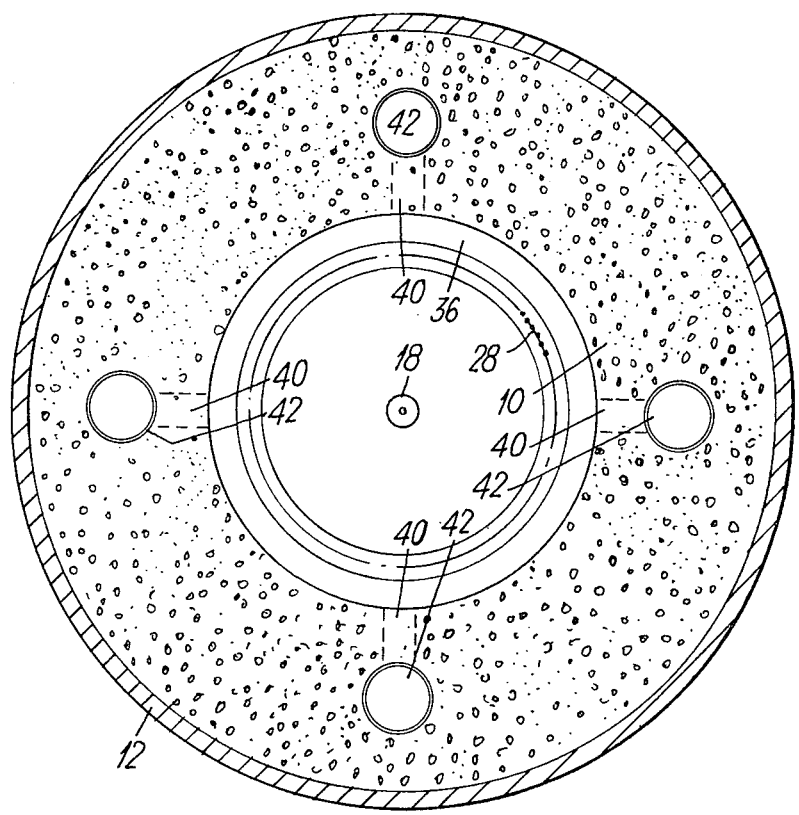

One plant according to the invention is shown in the accompanying drawing, in which FIG. 1 is a sectional elevation on an axial plane and FIG. 2 is a sectional plan across the upper part of the catalyst bed in FIG. 1.

The outer shell 10 of the vessel is formed of concrete and held together by pre-stressed wires 12 and vertical tie-rods(not shown). It is 96 feet high and 90 feet in diameter. The central chamber 14 is 60 feet high and 43 feet in diameter (volume 87300 ft$^3$, 2500 m$^3$), and it contains catalyst bed 16, 44 feet deep and 34 feet in diameter (volume 40000 ft$^3$, 1130 m$^3$), which in use is almost filled with particulate catalyst. Bed 16 is formed with an axial tube 18 leading from outside it at the bottom (space 32) to the space above the catalyst. The catalyst bed contains two sets of quench gas distributors of the hollow-bar type mentioned hereinbefore, which are fed from outside the vessel by gas inlet tubes 22.

Bed 16 has a perforated bottom and is supported within intermediate vessel 24, the annular space 26 between these vessels containing heat exchange tubes 28 (of which only a few are shown) which lead from space 30 above bed 16 to space 32 beneath it. Annular space 26 communicates at the top with outer annulus 34 which contains cooling tubes 36 fed with cooling water by tubes 38. Outer annuli 34 are formed each with at least one gas duct 40 feeding into compartments 42 each containing a gas circulator indicated generally by item 43, which feed back into space 30, into which fresh gas is fed by pipes 44. The bottom of each outer annulus 34 is a sump for the separated product, for which an outlet is provided by pipe 46. From the gas space of outer annulus 34 purge outlet 48 communicates with the exterior.

The drawings do not show means for gas heating at start-up or supplementary heating in operation, which are used on conventional plants; these could be incorporated in various forms either in an external by-pass or internally (eg. an electric heater could be placed in the central tube). Likewise means for charging or withdrawing catalyst and for temperature movement may be conventional.

The pre-stressed concrete shell has to be kept cool and, as is the practice with such vessels on nuclear energy installations, it would be either partially or fully lined with a metal liner incorporating a provision for cooling, instead of or in addition to the heat exchange and product recovery annuli as shown.

In operating the plant for methanol synthesis fresh synthesis gas (composition CO 11–12%, $CO_2$ 15–16%, $H_2$ 65–67%, $CH_4$ 6–7%,) compressed to for example 50 ata, is fed at about 30°C into space 30 where it mixes with recycled gas at the same temperature. The mixture, of composition CO 7–9.5%, $CO_2$ 13–15%, $H_2$ 54–56%, $CH_4$ 19.5–26%, passes through the tubes 28 of the heat exchanger and is heated to about 200°C, then via space 32 to tube 18 where it becomes heated to synthesis inlet temperature, suitably 220°C. It then enters the catalyst bed (suitably 60% Cu, 30% ZnO, 10% $Al_2O_3$ by metal atoms) and reacts to give methanol and sufficient heat to raise its temperature to 250°C at the level of the upper quench inlets 20, in which it meets fresh cold synthesis gas and is cooled to 220°C once more. The temperature rises to 250°C at the level of the lower quench inlets, is decreased by the cold gas to 220°C, then rises finally to 250°C at the bottom of the bed, which it leaves via space 24. The gas then enters the space about the heat exchanger tubes 28 and heats the gas within them and is cooled to 100°C. It is cooled to about 40°C in cooler 26, so that methanol condenses and is collected in the bottom of outer annulus 34. Separating baffles and possibly a water-spray are used to facilitate separation of the methanol. Gas passes out at 40 and is recirculated into space 34. Methanol is drawn off through pipe 46 and purge gas through pipe 48. Since the synthesis gas contains carbon dioxide, the methanol drawn off contains water, which may be removed by distillation. The methanol output is 7000 to 8000 metric tons per day.

The operation of the plant for ammonia synthesis is analogous but a promoted iron oxide catalyst is used and the synthesis gas composition is suitably $N_2$ 24.8%, $H_2$ 74.2%, inerts 1.0% (fresh) and $N_2$ 21.5%, $NH_3$ 2%, $H_2$ 64.5%, inerts 12.0% (as mixed with recycle gas). The catalyst inlet temperature is about 400°C and outlet temperature 480°C when the operating pressure is 150 ata. and correspondingly lower at the outlet at lower pressures at which the first plants of this type are likely to operate.

I claim:

1. A plant for catalytic exothermic gas phase conversion at superatmospheric temperature and pressure of synthesis gas to reacted gas producing a product recoverable in the liquid state and unreacted gas, which plant comprises:

an inner first vessel having closed top and side walls and a perforated bottom wall, said first vessel containing at least one bed of catalytic material, an intermediate second vessel positioned concentrically around and spaced from said inner first vessel, an axial conduit extending through said inner first and intermediate second vessels and extending above said catalytic material for directing synthesis gas to said bed of catalytic material, heat exchanger means mounted adjacent said inner first and intermediate second vessels for transferring heat from reacted gas emerging from said bed of catalytic material to the synthesis gas, cooling means mounted concentrically around said intermediate second vessel for condensing the product from said reacted gas, separator means mounted adjacent said cooling means for separating condensed product and the unreacted gas, an outer pressure vessel enclosing said inner first and intermediate second vessels, said heat exchanger means and said cooling means and being spaced therefrom so as to define a mixing zone said closed top of said inner first vessel, said outer pressure vessel having conduit means located therein, said conduit means communicating with said separator means and said mixing zone and having gas circulators mounted therein, said heat exchanger means having two portions, a first portion carrying the synthesis gas and a second portion carrying the reacted gas, said first portion communicating at one end with said axial conduit and at the other end with said mixing zone, said second portion communicating at one end with the perforated bottom of said inner first vessel and at the other end with said cooling means, synthesis gas inlet means extending from the exterior of said outer pressure vessel into said conduit means for inserting fresh synthesis gas into the plant, product withdrawal means for withdrawing said product from the plant extending from said separator means to the exterior of said outer pressure vessel.

2. A plant for catalytic exothermic conversaion of synthesis gas at superatmospheric temperature and pressure producing a product recoverable in the liquid phase and recycling unreacted gas for further conversion, which plant comprises:

an inner vessel containing at least one bed of catalytic material and having at least one inlet for synthesis gas and at least one outlet for reacted gas;

an intermediate vessel positioned coaxially around the said inner vessel and defining an inner annular space around said inner vessel;

a pressure-resisting shell enclosing the said intermediate vessel and defining an outer annular space around said intermediate vessel;

at least one compartment within the walls of the pressure-resisting shell;

a heat exchanger mounted within said inner annular space;

separator means for separating the product from unreacted gas, said separator means being mounted within said outer annular space;

at least one gas circulator in said at least one compartment, said circulator having an inlet and an outlet, a gas flow connection from the outlet of the gas circulator via the relatively cold side of the heat exchanger to the catalyst bed inlet;

a gas flow connection from the catalyst bed outlet via the relatively hot side of the heat exchanger to said separator means and thence to the gas circulator inlet;

at least one gas flow connection from the exterior of the pressure-resisting shell for introducing fresh synthesis gas into the plant; and at least one liquid flow connection extending from said separator means to the exterior of the pressure-resisting shell for withdrawing product from the plant.

3. A plant as claimed in claim 2 wherein said separator means comprises a cooling device for condensing the product from said gas emerging from said bed of catalytic material and separating baffles for collecting and separating the condensed product from unreacted gas.

4. A plant as claimed in claim 2 wherein coolant connections are provided on the exterior of said pressure-resisting shell to said cooling device so that coolant can be fed to withdrawn from said cooling device.

* * * * *